United States Patent [19]

Atkinson et al.

[11] Patent Number: 4,933,351
[45] Date of Patent: Jun. 12, 1990

[54] BENZOFURAN 2-CARBOX AMIDES USEFUL AS INHIBITORS OF LEUKORIENE BIOSYNTHESIS

[75] Inventors: Joseph G. Atkinson, Montreal; Yvan Guindon, Ile Bizard; Cheuk K. Lau, Pierrefonds, all of Canada

[73] Assignee: Merck Frosst Canada, Inc., Kirkland, Canada

[21] Appl. No.: 303,784

[22] Filed: Jan. 30, 1989

Related U.S. Application Data

[60] Division of Ser. No. 152,215, Feb. 4, 1988, Pat. No. 4,822,803, which is a division of Ser. No. 1,262, Jan. 7, 1987, Pat. No. 4,745,127, which is a division of Ser. No. 725,265, Apr. 19, 1985, Pat. No. 4,663,347, which is a continuation-in-part of Ser. No. 661,645, Oct. 17, 1984, abandoned, which is a continuation-in-part of Ser. No. 547,508, Oct. 31, 1983, abandoned.

[51] Int. Cl.$^5$ .................... A61K 31/34; C07D 307/85
[52] U.S. Cl. ........................ 514/320; 514/337; 514/382; 514/466; 514/469; 546/196; 546/269; 548/251; 549/435; 549/467
[58] Field of Search ................ 549/467, 435; 546/196, 546/269; 548/251; 514/337, 382, 466, 469, 320

[56] References Cited

U.S. PATENT DOCUMENTS

| | | | |
|---|---|---|---|
| 3,557,152 | 11/1971 | Zergenzi et al. | 549/460 |
| 3,574,208 | 4/1971 | Zergenzi et al. | 429/285 |
| 3,627,785 | 12/1971 | Zergenzi et al. | 549/468 |
| 3,646,047 | 2/1972 | Wright et al. | 546/196 |
| 3,651,094 | 3/1972 | Libis et al. | 549/468 |
| 3,665,074 | 5/1972 | Brandstrom et al. | 549/467 |
| 3,674,810 | 7/1972 | Zergenzi et al. | 549/467 |
| 3,723,619 | 3/1973 | Zergenizi et al. | 424/285 |
| 3,830,929 | 8/1974 | Nordmann et al. | 549/467 |
| 3,915,687 | 10/1975 | Braunling et al. | 71/88 |
| 4,055,117 | 10/1977 | Munday | 101/11 |
| 4,085,117 | 4/1978 | Cragoe Jr. et al. | 549/468 |
| 4,100,294 | 7/1978 | Cragoe, Jr. et al. | 424/275 |
| 4,213,998 | 7/1980 | Witiak | 424/285 |
| 4,221,793 | 9/1980 | Weber et al. | 544/376 |
| 4,229,467 | 11/1980 | Parker | 424/285 |
| 4,424,231 | 0/1984 | Bantick et al. | 549/468 |

FOREIGN PATENT DOCUMENTS

| | | |
|---|---|---|
| 671060 | 4/1966 | Belgium . |
| 19955 | 12/1980 | European Pat. Off. . |
| 45473 | 2/1982 | European Pat. Off. . |
| 73663 | 3/1983 | European Pat. Off. . |
| 69521 | 11/1983 | European Pat. Off. . |
| 123543 | 10/1984 | European Pat. Off. . |
| 1212984 | 3/1966 | Fed. Rep. of Germany . |
| 2909754 | 9/1980 | Fed. Rep. of Germany . |
| 2231372 | 2/1974 | France . |
| 50-35310 | 4/1975 | Japan . |
| 50-049270 | 5/1975 | Japan . |
| 56039015 | 9/1979 | Japan . |
| 57-040479 | 3/1982 | Japan . |
| 500966 | 2/1971 | Switzerland . |
| 540900 | 8/1973 | Switzerland . |
| 399106 | 9/1973 | U.S.S.R. . |
| 1008260 | of 0000 | United Kingdom . |
| 2118552 | of 0000 | United Kingdom . |
| 1233268 | 5/1971 | United Kingdom . |
| 1464242 | 2/1977 | United Kingdom . |
| 2007973 | 5/1979 | United Kingdom . |

OTHER PUBLICATIONS

Die Pharmazie 35, No. 9, pp. 517–539 (Sep. 1980).
Rene Rober et al., Eur, J. Med. Chem. Chimica Therapeutica, Mar.–Apr., 1974–9 No. 2 pp. 136–145.
W. B. Whalley, J. Chem. Soc., pp. 3229–3235 (1951).
Fujiwara et al., J. Org. Chem., 46, 851 (1981).
Chem. Abstracts, 65, 18546h.
Chem. Abstracts, 58, 13881c.
Chem. Ber., 99 (6), 2063–2065 (1966).
Rodighiero and Fornasiero, GAZZ. Chim. Ital., 91, 90–102 (1961).
Eur. J. Med. Chem.-Chim. Ther. 17, 577–580 (1982).
Grimev et al., C.A. 93:26184h.
Gaevai, V. P., C.A. 96:79444m.

Primary Examiner—Mary C. Lee
Assistant Examiner—Bernard I. Dentz
Attorney, Agent, or Firm—Gabriel Lopez; Hesna J. Pfeiffer

[57] ABSTRACT

Compounds of the Formula I:

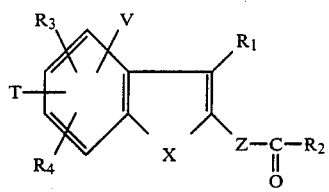

and pharmaceutically acceptable salts thereof are inhibitors of leukotriene biosynthesis. These compounds inhibit the mammalian 5-lipoxygenase enzyme, thus preventing the metabolism of arachidonic acid to the leukotrienes. These compounds are thus useful in the treatment of asthma, allergic disorders, inflammation, skin diseases and certain cardiovascular disorders.

5 Claims, No Drawings

BENZOFURAN 2-CARBOX AMIDES USEFUL AS INHIBITORS OF LEUKORIENE BIOSYNTHESIS

This is a division of Ser. No. 152,215, Feb. 4, 1988, U.S. Pat. No. 4,822,803, which is a division of Ser. No. 1,262, Jan. 7, 1987, U.S. Pat. No. 4,745,127, which is a division of Ser. No. 725,265, Apr. 19, 1985, U.S. Pat. No. 4,663,347, which is a continuation-in-part of Ser. No. 661,645, Oct. 17, 1984, abandoned, which is a continuation-in-part of Ser. No. 547,508, Oct. 31, 1983, abandoned.

U.S. Pat. No. 4,663,347 (Atkinson, et al.) is incorporated herein by reference in its entirety.

One embodiment of the present invention is a pharmaceutical composition containing a compound of the Formula I and an acceptable pharmaceutical carrier:

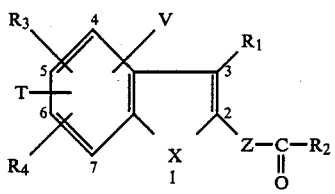

wherein:
Z is a bond, $CR_{14}=CR_{15}$ or $CHR_{14}-CHR_{15}$;
X is O, S, SO, or $SO_2$;
$R_2$ is H, OH, $C_1$ to $C_{20}$ alkoxy, including straight chain or branched chain, cycloalkyl, bicycloalkyl, tricycloalkyl or tetracycloalkyl;
$Ar_1$—$C_1$ to $C_3$ alkoxy;
$NR_8Ar_1$, wherein $R_8$ and $Ar_1$ can optionally be joined to form a heterocyclic ring having 5 to 8 atoms;
—$NR_8Het$;
—$N(R_8)CH_2Ar_1$;
—$N(R_{13})$—$N(R_{13})_2$ wherein each $R_{13}$ is independently hydrogen, $R_8$, $R_9$, $Ar_1$ or Het;
—NH—CH=C($Ar_1)_2$;
—$O(CH_2)_nNR_8R_9$ wherein n is 2 to 4;
—Z—$Ar_1$;

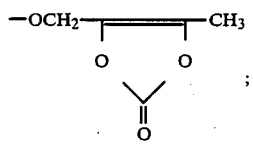

lower acyloxy-lower alkoxy

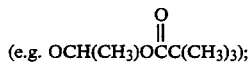

—$CH_2OH$;
—$(CH_2)_nAr_1$ wherein n is 0 to 3;
—$(CH_2)_nCOOR_6$ wherein n is 0 to 6;
$C_1$ to $C_{20}$ alkyl; $Ar_1$; Het; $(CH_2)_nNR_8R_9$ wherein n is 1 to 3; or
Het;

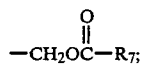

and $R_1$, $R_3$, $R_4$, T and V are each independently selected from:
(1) hydrogen;
(2) alkyl having 1 to 6 carbon atoms;
(3) alkenyl having 2 to 6 carbon atoms;
(4) —$(CH_2)_nM$ wherein n is 0 to 6 except when X is S and M is $OR_5$, in which case n is 1 to 6 and M is
(a) —$OR_5$;
(b) halogen;
(c) —$CF_3$;
(d) —$SR_5$;
(e) $Ar_1$;
(f) —$COOR_6$;
(g)

wherein $R_{12}$ is H, $C_1$ to $C_6$ alkyl, or $Ar_1$;
(h) tetrazole;

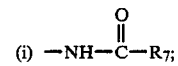

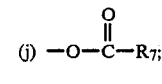

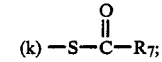

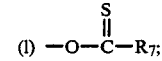

(m) —$NR_8R_9$;
(n) —$NHSO_2R_{10}$ wherein $R_{10}$ is OH, $C_1$ to $C_6$ alkyl, $CF_3$, $C_1$ to $C_6$-alkoxy, or $Ar_1$;

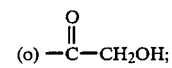

(p) —$SOR_5$;
(q) —$CONR_8R_9$;
(r) —$SO_2NR_8R_9$;
(s) —$SO_2R_5$;
(t) —$NO_2$; or
(u) —CN;
or any two of $R_3$, $R_4$, T and V may be joined to form a saturated ring having 5 or 6 ring atoms, said ring atoms comprising 0, 1 or 2 atoms selected from oxygen and sulfur, the remaining ring atoms being carbon;
each $R_5$ is independently H, $C_1$ to $C_6$ alkyl, benzyl, $Ar_1$, perfluoro-$C_1$ to $C_4$ alkyl, $CH_2$—$R_{11}$ wherein $R_{11}$ is $C_1$ to $C_5$ alkyldimethylamino, hydroxy-$C_2$ to $C_5$ alkyl, $CH_2COOR_6$, or $CH_2CO$—$R_7$;
each $R_6$ is independently H or $C_1$ to $C_6$ alkyl;
each $R_7$ is independently $C_1$ to $C_6$ alkyl, benzyl, $Ar_1$, $NR_8R_9$, $NHAr_1$, or O—$C_1$ to $C_4$ alkyl;
each $R_8$ and each $R_9$ is independently H or $C_1$ to $C_4$ alkyl, or $R_8$ and $R_9$ may be joined through the N to which they are attached to form a heterocycloalkyl ring having 5 to 8 ring atoms;

each Het is independently an aromatic heterocyclic ring having 5 or 6 ring atoms, one or more of which are selected from N, O and S;

each $Ar_1$ is independently 1- or 2- naphthyl, phenyl or mono- or disubstituted phenyl, wherein the substituents on the phenyl are independently selected from $C_1$ to $C_3$ alkyl, I, Br, Cl, F, $COOR_6$, $(CH_2)_n-NR_8R_9$ wherein n is 0 to 2, methylenedioxy, $C_1$ to $C_3$ alkoxy, OH, CN, $NO_2$, $CF_3$, $C_1$ to $C_4$ acyl, $NR_8R_9$, $S-C_1$ to $C_6$ alkyl, $SO-C_1$ to $C_6$ alkyl, and $SO_2-C_1$ to $C_6$ alkyl; and $R_{14}$ and $R_{15}$ are each independently H or $C_1$ to $C_6$ alkyl;

or a pharmaceutically acceptable salt thereof.

This invention also provides a method of treatment for disease states caused by the synthesis of the Leukotriences $C_4$, $D_4$, $E_4$ and $F_4$, as well as Leukotriene $B_4$, in mannals especially in a human subject. This method comprises administering to said subject an effective amount of a compound of Formula I combined with an appropriate pharmaceutical carrier.

The compounds of Formula I may be used to treat or prevent mammalian (especially human) disease states such as erosive gastritis; erosive esophagitis; inflammatory bowel disease; ethanol-induced hemorrhagic erosion; hepatic ischemia; noxious agent induced damage or necrosis of hepatic, pancreatic, renal, or myocardial tissue; liver parenchymal damage caused by hepatoxic agents such as $CCl_4$ and D-galactsoamine; ischemic rental failure; disease-induced hepatic damage; bile salt induced pancreatic or gastric damage; trauma- or stress-induced cell damage; and glycerol-induced rental failure.

Finally, this invention also provides novel compounds within the Formula I that act as inhibitors of the mammalian 5-lipoxygenase enzyme system, thus preventing the biosynthesis of the Leukotrienes $C_4$, $D_4$ and $E_4$ and also Leukotriene $B_4$.

What is claimed is:

1. A compound of the Formula:

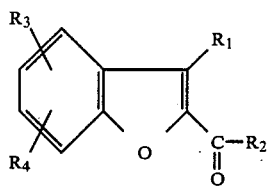

wherein the substituents for compound are selected from the following groups:

| Compound | $R_1$ | $R_2$ |
|---|---|---|
| 162 | $CH_3$ | —N(piperidinyl) |
| 163 | $CH_3$ | NHPh |
| 164 | $CH_3$ | NHPh-p-$NO_2$ |
| 165 | $CH_3$ | NHPh-p-OMe |
| 166 | $CH_3$ | NHPh-p-OMe |
| 167 | $CH_3$ | NHPh-p-$NO_2$ |
| 168 | $CH_3$ | NHPh-p-OMe |
| 169 | $CH_3$ | NHPh-p-$NO_2$ |
| 170 | $CH_3$ | —NH-(4-pyridyl) |
| 171 | $CH_3$ | NHPh |
| 173 | $CH_3$ | $NHCH_2Ph$ |
| 174 | $CH_3$ | NHPh-p-Cl |
| 175 | $CH_3$ | —NH-(2,3-methylenedioxy-phenyl-OCH2O) |
| 176 | $CH_3$ | —NH-(2,3-methylenedioxyphenyl) |
| 177 | Pr | NHPh-p-Cl |
| 178 | Ph | NHPh-p-Cl |
| 181 | $CH_3$ | —NH-tetrazolyl |
| 182 | Ph | NHPh-p-Cl |
| 183 | $CH_3$ | —NMePh |
| 184 | $CH_3$ | —NH-tetrazolyl |
| 185 | $CH_3$ | —NMePh |
| 186 | $CH_3$ | NHPh-p-OMe |
| 187 | $CH_3$ | —NH-(4-pyridyl) |
| 188 | Pr | NHPh-p-Cl |
| 189 | $CH_3$ | NHPh-p-Cl |
| 190 | $CH_3$ | NHPh-p-Cl |
| 191 | $CH_3$ | NHPh-p-OMe |
| 192 | $CH_3$ | NHPh-p-Cl |
| 193 | Pr | NHPh-p-Cl |
| 278 | $CH_3$ | —NH-triazolyl |

| Compound | $R_3$ | $R_4$ |
|---|---|---|
| 162 | 4-OH | H |
| 163 | 4-OH | H |
| 164 | 6-OH | H |
| 165 | 6-OH | H |
| 166 | 4-OH | H |
| 167 | 4-OAc | H |
| 168 | 4-OAc | H |
| 169 | 4-OH | H |
| 170 | 4-OH | H |
| 171 | 4-OAc | H |
| 173 | 4-OAc | H |
| 174 | 4-OAc | H |
| 175 | 4-OAc | H |
| 176 | 4-OH | H |

| | -continued | |
|---|---|---|
| 177 | 6-OH | H |
| 178 | 6-OAc | H |
| 181 | 5-OH | H |
| 182 | 6-OH | H |
| 183 | 4-OAc | H |
| 184 | 4-OH | H |
| 185 | 4-OH | H |
| 186 | 4-OH | 5-Pr |
| 187 | 4-OAc | H |
| 188 | 6-OAc | H |
| 189 | 4-OH | H |
| 190 | 4-O-C(=O)-OCH₃ | 5-CH₂CH=CH₂ |
| 191 | 4-O-C(=O)-OCH₃ | 5-Pr |
| 192 | 5-OH | H |
| 193 | 6-O-C(=O)-OCH₃ | H |
| 278 | 4-OH | H |

2. A method of inhibiting mammalian leukotriene biosynthesis or action which comprises administering to a mammal in need of such treatment a pharmaceutically effective amount of a compound of claim 1.

3. A method of claim 2 wherein the mammal is a human.

4. A method of treating pulmonary conditions, inflammation, allergies, pain, cardiovascular conditions, or skin conditions which comprises administering to a human in need of such treatment a pharmaceutically effective amount of a compound of claim 1.

5. A pharmaceutical composiiton useful for inhibiting the ibosynthesis of mammalian leukotrienes comprising a pharmaceuticlaly acceptable carrier and an effective amount of a compound of claim 1.

* * * * *